United States Patent [19]
Becker et al.

[11] Patent Number: 5,834,228
[45] Date of Patent: Nov. 10, 1998

[54] METHOD FOR IDENTIFYING INHIBITORS FOR APOPAIN BASED UPON THE CRYSTAL STRUCTURE OF THE APOPAIN: AC-DEVD-CHO COMPLEX

[75] Inventors: Joseph W. Becker, Bridgewater, N.J.; Donald W. Nicholson, Montreal, Canada; Jennifer Rotonda, Nutley; Nancy A. Thornberry, Westfield, both of N.J.; Kimberly M. Fazil, Markham, Canada; Michel Gallant, Montreal, Canada; Yves Gareau, Notre-Dame-De-Lile-Perrot, Canada; Marc Labelle, Ville Ile Perrot, Canada; Erin P. Peterson, Westfield, N.J.; Dita M. Rasper, Pierrefonds, Canada; Rejean Ruel, Pointe Claire, Canada; John P. Vaillancourt, Pierrefonds, Canada

[73] Assignees: Merck & Co., Inc., Rahway, N.J.; Merck Frosst Canada, Inc., Kirkland, Canada

[21] Appl. No.: 800,007

[22] Filed: Feb. 13, 1997

[51] Int. Cl.[6] .............................. C12Q 1/37; C12N 9/48
[52] U.S. Cl. ............................................. 435/23; 435/212
[58] Field of Search ....................................... 435/212, 23

[56] References Cited

FOREIGN PATENT DOCUMENTS

| 2 306 961 | 5/1997 | United Kingdom . |
|---|---|---|
| WO 95/35367 | 12/1995 | WIPO . |
| WO 96/33268 | 10/1996 | WIPO . |
| WO 97/00895 | 1/1997 | WIPO . |
| WO 97/06246 | 2/1997 | WIPO . |
| WP 97/08300 | 3/1997 | WIPO . |

OTHER PUBLICATIONS

Casciola–Rosen, et al., "Apopain/CPP32 Cleaves Proteins that are Essential for Cellular Repair . . .", J. of Exp. Med., vol. 183, pp. 1957–1964, 1996.
Darmon, et al., "Activation of the apoptotic protease CPP32 by cytotoxic T–cell–derived granzyme B", Nature, vol. 377, pp. 446–448, 1995.
Nicholson et al. (1995) Nature, 376, "Identification and Inhibition of the ICE/CED–3 Protease Necessary for Mammalian Apoptosis", pp. 37–43.
Dixon (1992) Trends Biotech., 10(10), "Computer–Aided Drug Design: Getting the Best Results", pp. 357–363.
Appelt et al. (1991) J. Med. Chem., 34(7), "Design of Enzyme Inhibitors Using Iterative Protein Crystallographic Analysis", pp. 1925–1934.
Broom (1988) J. Med. Chem., 32(11), "Rational Design of Enzyme Inhibitors: Multisubstrate Analogue Inhibitors", pp. 2–7.
McPherson (1990) Eur. J. Biochem., 189, "Current Approaches to Macromolecular Crystallization", pp. 1–23.
Eisenberg et al. (1989) Trends Biotechnol., 14, "Protein Crystallography: More Surprises Ahead", pp. 259–264.
Rotonda et al. (1996) Nat. Struct. Biol., 3(7), "The Three–Dimensional Structure of Apopain/CPP32, a Key Mediator of Apoptosis" pp. 619–625.

*Primary Examiner*—Jon P. Weber
*Attorney, Agent, or Firm*—Joseph A. Coppola; Jack L. Tribble

[57] ABSTRACT

The apopain:Ac-DEVD-CHO complex has been crystallized and its structure determined by x-ray crystallography. Based upon this crystal structure of the complex, a method for identifying inhibitors of apopain is presented which comprises designing putative inhibitors having specific contacts with apopain, making the putative inhibitors, and testing the putative inhibitors for their ability to inhibit apopain.

8 Claims, 6 Drawing Sheets

```
icel                      sqgvlssfpa pqavgdnpam ptssgseGNV KLCSLEEAAQR IWKQKSAEIY
apop                                                                    ****
                                 160        170        180        190        200
icel  .........  .........  .........  .........  .........sgisldnsYKMDY
apop  PIMDKSSRTR LALIICNEEF DS..IPRRT GAEVDITGMT MLLQNLGYSV
      ***        *          *          ******     **********
                                 210        220        230        240        250
icel  PEM......GL CIIINNKNFH KSTGMTSRS GTDVDAANLR ETFRNLKYEV
apop  DVKKNLTASD MTTELEAFAH RPEHKTSDST FLVFMSHGIR EGICGKKHSE
                            ab
      **         *********  **         **********  **********
                                 260        270        280        290        297
icel  RNKNDLTREE IVELMRDVSK ED.HSKRSSF VCVLSHGEE GIIFGTN....
apop  QVPDILQLNA IFNMLNTKNC PSLKDKPKVI IIQACRGDSP GVVWFKD
      **********  **********  **        **********  *******
                                 320        330        340        350        360
icel  ...GPVDLKK ITNFFRGDRC RSLTGKPKLF IIQACRGTEL DCGIEtd
apop  ........AIKKAH IEKDFIAFCS STPDNVSWRH PTMGSVFIGR LIEHMQEYAC
      *              **********  **********  **********  **********
                                 370        380        390        400
icel  sgvdddmaCHKIP VEADFLYAYS TAPGYYSWRN SKDGSWFIQS LCAMLKQYAD
apop  SCDVEEIFRK VRFSFEQ.PD ..........G RAQMPTTERV TLTRCFYLFP
      **********  ****                   **********  **********
icel  KLEFMHILTR VNRKVATEFE SFSFDATFHA KKQIPCIV.S MLTKELYFYH
apop  **********  **********  **********  ********  **********
                                          abcdefghi
                                          a

404
      GH icel
apop
```

FIG. 1C

METHOD FOR IDENTIFYING INHIBITORS FOR APOPAIN BASED UPON THE CRYSTAL STRUCTURE OF THE APOPAIN: AC-DEVD-CHO COMPLEX

FIELD OF THE INVENTION

Apoptosis

BACKGROUND OF THE INVENTION

The present invention relates to crystalline apopain, the structure of apopain as determined by X-ray crystallography, the use of that structure to solve the structure of apopain homologues and other crystal forms of apopain, mutants and co-complexes of apopain, and the use of the apopain structure and that of its homologues, mutants, and co-complexes to design modulators of apopain.

One aspect of the invention resides in the obtaining of crystals of apopain of sufficient quality to determine the three dimensional (tertiary) structure of the protein by X-ray diffraction methods. Obtaining such crystals is in fact very much an unexpected result. It is well known in the protein crystallographic art that obtaining crystals of quality sufficient for determining the structure of the apopain has not been achievable until the present application. Accordingly, one object of the present invention is to provide crystals of sufficient quality to obtain a determination of the three-dimensional structure of apopain to high resolution. The value of the crystals of apopain extends beyond merely being able to obtain a structure for apopain alone. The knowledge obtained concerning apopain may be used to model the tertiary structure of related proteins. Another aspect of the present invention is to provide a starting material for use in the determination of the structure of other members of the apopain family of proteins. The knowledge of the structure of the apopain family of proteins provides a means of investigating the mechanism of action of these proteins in the body. For example, binding of these proteins to various receptor molecules can be predicted by various computer models. Upon discovering that such binding in fact takes place, knowledge of the protein structure then allows chemists to design and attempt to synthesize small molecules which mimic the functional binding of apopain to its receptor. This is the method of "rational" drug design. Accordingly, another aspect of the invention is to provide material which is a starting material in the rational design of drugs which mimic the action of apopain.

Cysteine proteases related to mammalian interleukin-1β converting enzyme (ICE) and to CED-3—the product of a gene required for programmed cell death in the nematode *C. elegans*—have been shown to play a critical role in the biochemical events that culminate in apoptosis in vertebrates[1–3]. Several human isoforms of the ICE/CED-3-like protease family, which divide into two distinct phylogenic subfamilies, have now been identified. Those related to ICE include $ICE_{rel}$-II (TX, ICH-2) and $ICE_{rel}$-III, and those more similar to CED-3 include ICH-1 (mNedd2), CPP32 (apopain, Yama), Mch2 and Mch3 (ICE-LAP3))[4–14]. We have determined the three-dimensional structure of a complex of CPP32/apopain with a potent tetrapeptidealdehyde inhibitor by X-ray diffraction analysis. The protein is similar to ICE in tertiary and quaternary structure as well as in the features associated with its catalytic activity. The $S_4$ subsite of apopain, however, is strikingly different from that of ICE in size and chemical composition. These differences provide a structural basis for understanding the differences in specificity between the two subfamilies of these enzymes.

Although a role for ICE itself in mammalian apoptosis has yet to be definitively established[15, 16], it is clear that at least one homologue, apopain/CPP32, is a key player in this important physiological process[17–20]. Apopain incapacitates key homeostatic and repair enzymes at the onset of apoptosis by separating essential functional domains at $(P_4)$Asp-X-X-Asp$(P_1)$ (SEQ ID NO:9) motifs. Known substrates for apopain include poly(ADP-ribose) polymerase (an enzyme involved in genome surveillance and DNA repair in stressed cells), the U1–70 kDa small nuclear ribonucleoprotein (which is necessary for mRNA splicing) and the 460 kDa catalytic subunit of the DNA-dependent protein kinase (which is essential for DNA double-strand break repair)[15, 19, 21–23]. Additional potential substrates for apopain and apopain-like proteases during cell suicide include structural proteins, such as fodrin (non-erythroid spectrin), nuclear lamins and growth arrest-specific protein 2 (Gas2), as well as protein kinase C and several as-yet-unidentified lupus autoantigens[22, 24–27]. These proteases thus appear to participate in a cascade of cleavage events that contribute to the disabling of homeostatic and repair processes as well as the systematic structural disassembly of dying cells. An imbalance in apoptosis appears to underlie the etiology of many human diseases that may involve both insufficient apoptotic death, such as cancer, as well as excessive or premature apoptosis, such as Alzheimer's disease. Thus, the identification of specific biochemical mediators of apoptosis, such as apopain, opens the possibility for therapeutic intervention in these diseases.

ICE/CED-3 proteases all appear to be synthesized as proenzymes each of which is proteolytically processed to form a heterodimeric catalytic domain. In the recently published crystal structure of ICE, two heterodimers associate to form a tetramer, an observation that has led to the suggestion that this species is the catalytically active form of the enzyme[28, 29]. The most distinctive catalytic property of this family is a near absolute requirement for Asp at the substrate $P_1$ position[4, 5, 28–30]. Despite these and other similarities, however, the substrate specificity for ICE and apopain are markedly different. ICE has a preference for hydrophobic residues in the $P_4$ position, a critical determinant, while apopain appears to be specific for Asp in this position. We therefore sought to determine the three-dimensional structure of apopain to identify the determinants that account for this striking difference in substrate specificity, to provide a foundation for the design of highly-specific modulators of this enzyme, and ultimately to understand the structural basis for the role of apopain and functionally-related family members in apoptotic cell death.

We have solved the three-dimensional structure of apopain in complex with the peptide-aldehyde inhibitor Ac-DEVD-CHO (SEQ ID NO:10) at a nominal resolution of 2.5 Å. The tertiary and quaternary structures of apopain are strikingly similar to those of ICE (FIG. 1). The p17 and p12 subunits of apopain are folded into a compact cylinder approximately 40×33×25 Å in size, and the folding is dominated by a central 6-stranded β-sheet with five parallel and one antiparallel strands. There is a small two-stranded antiparallel β-sheet at the top of the cylinder that is part of the modulator-binding site and a second two-stranded antiparallel β-sheet at the front of the molecule (FIG. 1A). In addition, there is a very small two-stranded β-structure that involves the C-terminus of the p17 subunit and the N-terminus of the p12 subunit (see discussion of quaternary structure below). There are five helices, three on one side of the main β-sheet and two on the other side. The helix at the N-terminus of the p20 subunit of ICE (FIG. 1B) does not have an equivalent in the apopain crystal structure, and the residues corresponding to this helix in the aligned amino acid of apopain are apparently disordered in the crystal structure. As in the ICE structure, pairs of p17–p12 heterodimers are assembled into discrete tetramers in the crystal lattice by extending the central β-structure across a crystallographic axis of two-fold rotational symmetry (FIG. 2). The inhibitor is in an extended conformation, and its binding to the enzyme is quite similar to the binding of tetrapeptide aldehyde inhibitors to ICE. The mode of binding involving the $P_1$–$P_3$ residues of the inhibitor are quite similar to those observed in the ICE structures, but the interactions involving the Asp residue at $P_4$ are significantly different, consistent with the differing specificities of the two enzymes at this position.

When the apopain and ICE structures are aligned on 194 residues with similar secondary structure or conformation, the average difference between equivalent alpha carbon atoms is 1.11 Å. The most significant differences in the overall structures of the two enzymes are that apopain lacks two small surface loops that are present in ICE and contains one extra loop not present in the other enzyme. Missing from apopain are groups equivalent to residues 156–160 (bottom left of FIG. 1B) and 248–258 (top center of FIG. 1B) of ICE. Apopain contains a ten-residue insert at a position equivalent to residue 381 of ICE (top right of FIG. 1A) and this extra loop forms an irregular reverse turn over the bound inhibitor and contributes several residues that make up part of the binding site; addition of this loop is one of the most significant differences between the two classes of ICE-related proteases exemplified by these two enzymes. For example, all members of the ICE subfamily (ICE, $ICE_{rel}$-II, $ICE_{rel}$-III) are predicted not to have this loop based on primary sequence alignment, whereas all members of the CED-3-like subfamily, including C. elegans CED-3 itself, are predicted to have an equivalent loop (e.g. ICH-1, Mch2, Mch3). The presence of this loop structure therefore appears to be a molecular signature indicating structural and probably functional relatedness to apopain (see below).

The quaternary structures of the two enzymes are, in general, quite similar. In each protein, the heterodimer formed by the two chains associates closely with a structurally identical heterodimer to form a four-chain assembly with two-fold rotational symmetry. In both proteins, the central β-sheet extends across the resulting interface and anti-parallel β-structure-type hydrogen bonds involving residues 389 and 392 join the two heterodimers. The resulting tetrametic assembly is approximately 50×35×25 Å in size with a 12-stranded β-structure running through its center, and contains two catalytic sites at widely-separated parts of the molecule (FIG. 2). When the two tetramers are aligned, the equivalent 388 alpha carbons differ by an average of only 2.01 Å. The observation that ICE and apopain adopt such similar quaternary structures in two different crystal lattices lends support to the notion that this structure may be common to other members of this family of enzymes.

In apopain, as in ICE, the C-terminus of the larger subunit of a heterodimer is quite distant (52 Å) from the N-terminus of the smaller subunit of the same heterodimer. For example, residue 295 of the dark left p17 chain in FIG. 2 is 52 Å from the residue 317 of the light left p12 chain. This distance is too long to be spanned by the nine residues that link these residues in the apopain precursor but are disordered in the crystal structure. For this reason, the folding and processing of apopain must, like that of ICE, involve some unusual features. For both proteins, two models can be proposed[28, 29]. In the first model, the dark p17 chain (left of FIG. 2) derives from the same precursor molecule as the dark p12 chain (right of FIG. 2). These residues are only 12 Å apart, and they can easily be connected by the nine disordered residues without any major structural rearrangement. However, this model requires that the relatively compact heterodimers seen in the mature proteins (FIG. 1) must derive from two separately synthesized and folded polypeptide chains. In both the ICE and apopain structures, this model is supported by the contiguity of the new chain termini. In the ICE structure, this model is also supported by the fact that there are extensive β-structure hydrogen bonds between the C-terminus of the subunit corresponding to the dark p17 chain of FIG. 2 (left) and the N-terminus of the dark p12 chain. These interactions connect residues 291–297 of the p20 chain to residues 317–323 of the p10 chain and involve seven hydrogen bonds. In apopain, however, the corresponding interaction is much less extensive: the β-structure involves only two residues from each chain ($Gly^{293}$, $Ile^{294}$, $Ile^{321}$, $Pro^{322}$) and two hydrogen bonds.

In the second model, the two chains at the left of FIG. 2, the dark p17 chain and the light p12 chain are derived from the same p32 precursor. This model is supported by the notion that the relatively compact heterodimer at the left of FIG. 2 is derived from a single precursor molecule, but it requires a relatively large conformational change upon processing. In the apopain structure, such a change would have only local effects and would not affect the overall structure of the protein. One can imagine that in the apopain precursor, a surface loop connects the C-terminus of the blue subunit with the N-terminus of the red chain. Such a loop would extend from the end of the β-strand comprising residues 278–283 (fourth from the left in FIG. 2) to the beginning of the strand spanning residues 327–331 (fifth from the left in FIG. 2), and the precursor would have the same tertiary and quaternary structure as the mature protein with the exception of the small β-structure involving residues 293–294 and 321–322. The feasibility of this model is supported by the fact that even larger and more radical conformational changes are known to follow proteolysis in the serpin family[31, 32]. The ICE and apopain structures, in themselves, do not rigorously exclude either model. In summary, the arrangement of subunits and specific residues involved in precursor processing are quite similar in both ICE and apopain, but knowledge of the precise details of the structure of the precursors of apopain and ICE and their processing must await more definitive studies The active site of apopain and the details of its interactions with the tetrapeptide aldehyde inhibitor, Ac-Asp-Glu-Val-Asp-CHO (SEQ ID NO:10), are similar to the analogous features of the ICE:Ac-Try-Val-Ala-Asp-CHO (SEQ ID NO:11) complex with the exception of the $S_4$ subsite, where the two proteins differ profoundly. In both proteins, the inhibitor is bound in a groove in the enzyme surface. The sidechains at $P_1$ and $P_4$ are contained in pronounced depressions in the binding groove where they make numerous interactions with the protein, while the $S_2$ and $S_3$ sidechains point away from the body of the protein. In both complexes, there are three anti-parallel β-structure-like hydrogen bonds between the inhibitor backbone and the enzyme: $P_1$ O-$Ser^{339}$ N, $P_2$ N-$Arg^{341}$ O, and $P_2$ O-$Arg^{341}$ N (FIG. 3). The $S_1$ subsite is remarkably similar in the ICE and apopain complexes. The carbonyl carbon atom of $P_1$ is bound to the Sγ of the $Cys^{285}$ and the side chain of this residue is involved in a complicated series of polar interactions with the side chains of $Arg^{179}$, $Gln^{283}$, and $Arg^{341}$. The striking similarity of the three-dimensional structures of apopain and ICE at the sites of their catalytic activity strongly suggests that the details of the catalytic mechanisms of these proteins will be preserved. The fact that all of the residues implicated by the structure in catalysis and in $S_1$ are conserved among members of the ICE/CED-3 protease family suggests that these enzymes will share a common mechanism of catalysis, and a nearly absolute requirement for Asp in $P_1$.

The local concentration of the two positive charges of the arginyl side chains in $S_1$ is stabilized by the negatively-charged aspartyl side chain of the modulators and substrates of these enzymes. It is quite likely that the conformation observed in the three-dimensional structures of inhibited apopain and ICE would be unstable in the uninhibited enzymes, where such stabilization is absent. These observations suggest either that the free enzyme contains a counterion such as acetate or several water molecules in $S_1$, or that there is a significant local conformational change on the binding or release of modulators and substrates.

Differences between the apopain and ICE complexes at $S_2$ and $S_3$ primarily arise from amino acid sequence differences. In apopain, the side chains of the $P_3$ glutamyl residue points away from the body of the protein, but makes a salt link to the side chain of $Arg^{341}$, consistent with the specificity of the enzyme at this site. The $Arg^{341}$ side chain also interacts with the $P_1$ aspartyl side chain (see above). The side chain of the $P_2$ valine lies against a hydrophobic wall of the groove centered on the side chain of $Tyr^{338}$.

Unlike the similarities between apopain and ICE in $S_1$–$S_3$, the $S_4$ subsites differ radically in both their overall geometry and their chemical nature. The $S_4$ subsite of ICE is a large and shallow hydrophobic depression that easily accommodates a tyrosyl side chain, while the corresponding site in apopain is a narrow socket that closely envelops the $P_1$ Asp sidechain. When the two sites are compared, the most obvious differences are the constriction of the apopain site caused by the presence of the sidechains of $Trp^{348}$ and $Phe^{380A}$ (FIG. 4). In addition, the volume occupied by the sidechain of $Arg^{383}$ in ICE is filled with the inserted peptide that starts at $Ser^{381A}$. This peptide extends from well within $S_4$ to well beyond the surface of the protein.

The $S_4$ subsite of apopain affords an understanding of the specificity of the enzyme at this position. The site is delimited by $Trp^{340}$, $Arg^{341}$, $Asn^{342}$, $Trp^{348}$, $Ser^{381A}$ and $Phe^{381B}$ (FIG. 4A). The carboxyl group of the inhibitor makes specific polar interactions with the amide nitrogen atom of $Phe^{381B}$ and the $N^{\delta 1}$ atom of $Asn^{342}$. This network of hydrogen bonds is extended by an interaction between the $Asn^{342}$ $N^{\delta 2}$ atom and the amide nitrogens of $Lys^{344}$ and $Asp^{345}$. The site is complementary in size and shape to an aspartyl side chain, and it contains two hydrogen bond donors firmly positioned with the appropriate geometry to interact with a carboxyl group. The orientation of the side chain of $Asn^{342}$ is fixed by the interactions of its $O^{\delta 1}$, a hydrogen bond acceptor, with amide nitrogens of $Lys^{344}$ and $Asp^{345}$, hydrogen bond donors. The Trp residue at position 348 and the inserted ten amino acid residues at position 380, which play a crucial role in defining the size and shape of the $S_4$ subsite of apopain, are absolutely conserved in the known CED-subfamily of ICE-related proteases suggesting that these enzymes will have similar specificities at this subsite.

The three-dimensional structure of apopain is generally similar in tertiary and quaternary structure to that of ICE. In addition these two proteins interact with analogous modulator peptides in very similar ways in the $S_1$–$S_3$ subsites. However, there are dramatic differences in the size and nature of the $S_4$ subsites consistent with the amino acid sequence variation and substrate specificity differences between these two enzymes. These differences provide a foundation for understanding the structural and functional differences between the two subfamilies of the ICE-specific proteases that these enzymes exemplify. In addition, comparison of these two structures provides a structural basis for the design of highly specific modulators of these proteins that will be of great value in the study of the disease states and physiological functions with which they are associated.

SUMMARY OF THE INVENTION

The present invention relates to crystalline apopain, the structure of apopain as determined by X-ray crystallography, the use of that structure to solve the structure of apopain homologues and other crystal forms of apopain, mutants and co-complexes of apopain, and the use of the apopain structure and that of its homologues, mutants, and co-complexes to design modulators of apopain.

In one aspect the present invention is directed to the three-dimensional structure of an isolated and purified enzyme designated apopain and its structure coordinates. Another aspect of the invention is to use the structure coordinates of the apopain crystal to reveal the atomic details of the active site and one or more of the accessory binding sites of apopain. Another aspect of the invention is to use the structure coordinates of an apopain crystal to solve the structure of a different apopain crystal or crystal of a mutant, homologue or co-complex of apopain. A further aspect of the invention is to provide apopain mutants characterized by one or more different properties compared to wild-type apopain. Another aspect of this invention is to use the structure coordinates and atomic details of apopains or mutants or homologues or co-complexes thereof to design, evaluate computationally, synthesize and use modulators of apopain that prevent or treat the undesirable physical and pharmacological properties of apopain. These modulators may be used as therapies that are beneficial in the treatment of immune, proliferative and degenerative diseases including, but not limited to, immune deficiency syndromes (such as AIDS), autoimmune diseases, pathogenic infections, cardiovascular and neurological injury, alopecia, aging, cancer, Parkinson's disease, Alzheimer's disease, Huntington's disease, neurodegenerative disorders and spinal cord injury.

In a second aspect, this invention relates to compounds of formula I (designated L-761,191):

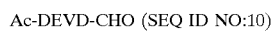

Ac-DEVD-CHO (SEQ ID NO:10)                    I useful as research tools in the field of apoptosis, as well as in the treatment of diseases in which reduced apoptosis would be beneficial, including, but not limited to those listed above. In particular, this invention relates to modulators of the pro-apoptotic proteolytic activity of thiol proteinases which cause apoptosis at least in part by disabling the normal biological function of poly(ADP-ribose)polymerase, U1–70 kDa small ribonucleoprotein and the catalytic subunit of DNA-dependent protein kinase.

BRIEF DESCRIPTION OF THE DRAWINGS

FIG. 1(C) shows the amino acid sequences of apopain and ICE aligned by matching residues that have similar secondary structures or conformations in the aligned three-dimensional structures of the two proteins. Lower-case letters represent residues for which no electron density is evident. To facilitate comparison between ICE and apopain, the amino acid residues of apopain are identified by the sequence numbers of the homologous residues in ICE in this alignment. Apopain sequence numbers are omitted when no ICE-related residue is present in apopain, and apopain-specific insertions are indicated by the additions of letters to the ICE sequence numbers.

Figure 1B:
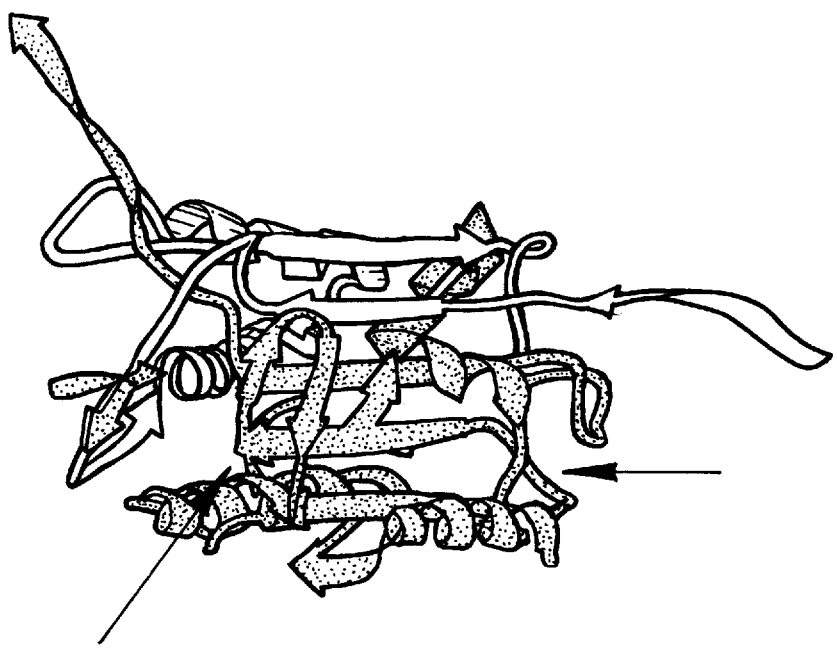
FIG. 1(B) shows the ICE:YVAD (SEQ ID NO:11) structure oriented to maximize alignment with (A). The two extra loops in ICE are indicated by the white arrows at the bottom (residues 156–160) and top left (residues 248–253) of the figure. The p20 chain is dark; the p10 chain, light.

The method used for production of apopain involves folding of active enzyme from its constituent p17 and p12 subunits which are expressed separately in E. coli. Amino acid numbering for the purpose of the recombinant engineering described in this section refers to amino acid positions within the apopain proenzyme as determined from the open reading frame of GenBank accession number U13738 (the initiator methionine being residue 1 and the final residue preceding the stop codon being residue 402). The beginning and end of each subunit was determined by mass spectroscopy analysis and amino-terminal microsequencing of non-recombinant, purified human apopain.[19] The apopain/CPP32 p17 subunit ($Ser^{141}$-$Asp^{297}$) and p12 subunit ($Ser^{310}$-$His^{402}$) were engineered for expression as $MetSer^{141}$-$Asp^{297}$ and $MetSer^{310}$-$His^{402}$ constructs, respectively, by PCR-directed template modification. A cDNA encoding the p17 subunit was amplified with the sense (forward) synthetic oligonucleotide 5'-GCT CTA GAC TCG AGT CAT GAG TGG AAT ATC CCT GGA CAA CAG TTA TAA AAT GG -3' (SEQ ID NO:1) plus the antisense (reverse) oligonucleotide 5'- GCT CTA GAC TCG AGT CAT GAT TAG TCT GTC TCA ATG CCA CAG TCC AGT TCT G -3' (SEQ ID NO:2) using the full length CPP32β cDNA (3 ng/μl) as template (Pwo polymerase (0.025 U/μl) Boehringer Mannheim; 25 cycles of 1 min at 94° C., 1 min at 60° C., 45 sec at 72° C.). A cDNA encoding the p12 subunit was amplified the same way except that the sense (forward) oligonucleotide was 5'- GCT CTA GAC TCG AGT CAT GAG TGG TGT TGA TGA TGA CAT GGC GTG TC -3' (SEQ ID NO:3) and the antisense (reverse) oligonucleotide was 5'- GCT CTA GAC TCG AGT CAT GAT TAG TGA TAA AAA TAG AGT TCT TTT GTG AGC -3' (SEQ ID NO:4). The resulting PCR fragments were purified, trimmed with Xba I then ligated into the Xba I site of pBluescript II SK(+) (Stratagene). Following sequence verification, inserts were excised from nested Bsp HI sites and ligated into the Nco I site of pET-11d (Novagen). Appropriately oriented clones were then transformed into E. coli BL21(DE3)pLysS cells. Optimal growth conditions for production cultures employed M9 medium at 37° with overnight induction using 1 mM IPTG for expression of the recombinant proteins. (Under these conditions, the individual subunits were expressed at approximately 50 mg/liter. In both cases the protein was localized exclusively in the inclusion body fraction where they generally constituted>99% of the total protein.) The E. coli were harvested, washed, and broken in the presence of protease inhibitors. The inclusion bodies were then isolated and solubilized in 6M guanidine-hydrochloride. In order to generate active recombinant apopain, the denatured p17 and p12 subunits were mixed and rapidly diluted to a concentration of 100 μg/ml in 100 mM HEPES/KOH (pH 7.5) 10% (w/v) sucrose, 0.1% (w/v) CHAPS, 0.5M NaCl, 10 mM DTT. (Several pilot experiments have established these to be the optimal folding conditions.) The reactions were then incubated at room temperature for 60 min. Under these conditions some of the subunit protein precipitated; this was removed by ultracentrifugation at 100,000×g for 60 min. Using this method, the efficiency of refolding was approximately 10% (mole active enzyme/mole p17 subunit×100%) which corresponds to a total yield of approximately 5 mg active enzyme/liter culture. The active enzyme was subsequently separated from incorrectly folded protein by anion-exchange chromatography using a 1 ml HiTrap Q column (Pharmacia). Mass spectral analysis of recombinant apopain complex indicates that it comprises intact p17 chains, spanning $Ser^{141}$ to $Asp^{297}$, and a mixture of p12 chains, consisting of predominantly $MetSer^{310}$-$His^{402}$ with some $Ser^{310}$-$His^{402}$. The resulting enzyme is indistinguishable from native enzyme with regard to kinetic parameters for inhibition by Ac-DEVD-CHO (SEQ ID NO:10).

The apopain:Ac-DEVD-CHO (SEQ ID NO:10) complex was crystallized by hanging-drop vapor diffusion. 1.5 μl drops of protein-inhibitor solution (8.7 mg/ml in 10 mM Tris-HCl pH 8.5, 10 mM DTT, 3 mM $NaN_3$) were mixed with an equal volume of reservoir buffer (7% PEG-6000 (w/w), 0.10M sodium citrate pH 5.0, 10 mM DTT, 3 mM $NaN_3$) and incubated at room temperature. The crystals belong to the orthorhombic space group I222 with a=69.81, b=84.62, c=96.79 Å. Three-dimensional diffraction data extending to a resolution of 2.5 Å were collected at room temperature using a Siemens area detector and CuKα radiation from a Rigaku RU-200 rotating-anode X-ray generator. These data were processed with the SAINT software package[36]. 20,801 observations of 8.929 unique reflections were merged with an R-factor of 5.55%. The structure was solved by molecular replacement, using X-PLOR[37] and a model based on PDB[38] entry 1ICE, the structure of inhibited ICE[28]. The current model was constructed by interactive model-building[39] and refinement using X-PLOR[37]. In early stages of model-building, phase refinement using SQUASH[40] significantly improved the quality of electron density maps. The current model was inspected against 10% simulated-annealing omit maps[41] and comprises residues 149–295 of the p17 chain, residues 317–402 of the p12 chain, the bound inhibitor, and 25 ordered water molecules. Residues 141–148 at the N-terminus of the p17 chain, 296–297 at the C-terminus of the p17 chain, and 310–316 at the N-terminus of the p12 chain are not visible in the current electron density maps, presumably due to disorder. The R-factor of the refined model is 26.2% ($R_{free}$=34.2%)[42] and the stereochemistry is reasonable (r.m.s. deviation of bonds=0.006 Å, angles=1.3°). Secondary structures were assigned to both apopain and ICE using the program STRIDE[43]. Special care was taken to establish the chirality at the optical center created by the nucleophilic attack of $Cys^{285}$ Sγ at the $P_1$ carbon atom. After refinement was completed, equivalent models were constructed for each possible configuration at this atom and the two models were refined in parallel with chiral restraints that were identical in magnitude, but opposite in hand. Then, all atoms within 8.0 Å of this atom were deleted from each model and both truncated models were subjected to a 3000K simulated-annealing refinement. Electron density maps of this part of the complex were then calculated from both sets of phases and inspected to determine the stereochemistry at this site. The coordinates and structure factors of the apopain:Ac-DEVD-CHO (SEQ ID NO:10) complex will be deposited in the Protein Data Bank[38].

Figure 1A:
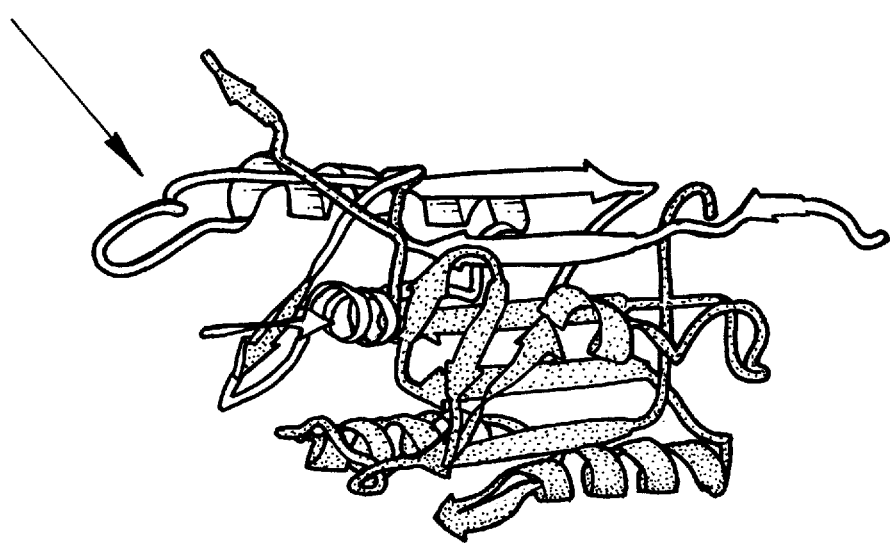
FIG. 1(A) is a schematic representation of the apopain:Ac-DEVD-CHO (SEQ ID NO:10) structure viewed down the crystallographic two-fold axis. β-structures are arrows; α-helices, coils. The bound inhibitor is represented by the short arrow at the top of the figure. The extra loop (residues 180A, 181A–I) in apopain is indicated by the arrow. The p17 chain is dark; the p12 chain, light.
Figure 2:
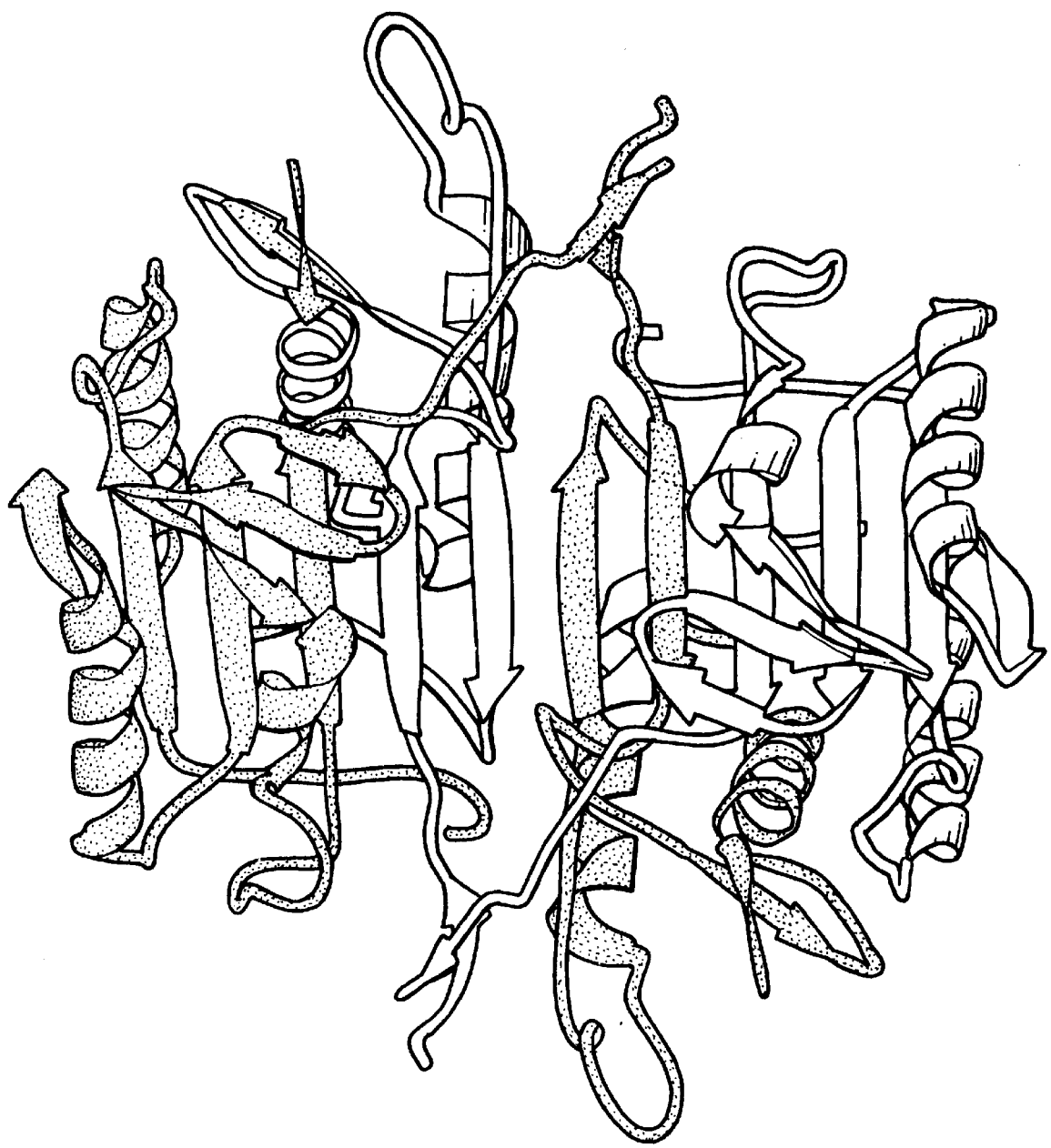

FIG. 2 is a schematic representation of the apopain tetramer oriented as in FIG. 1. The heterodimer at the left of the figure is identical to FIG. 1A. In the left-hand heterodimer, the p17 chain is colored dark; the p12 chain light. The colors are reversed in the heterodimer at the right. The bound inhibitor molecules are the short arrows at the top of the dimer on the left side of the figure and the bottom of the dimer on the right.

Figure 3A:
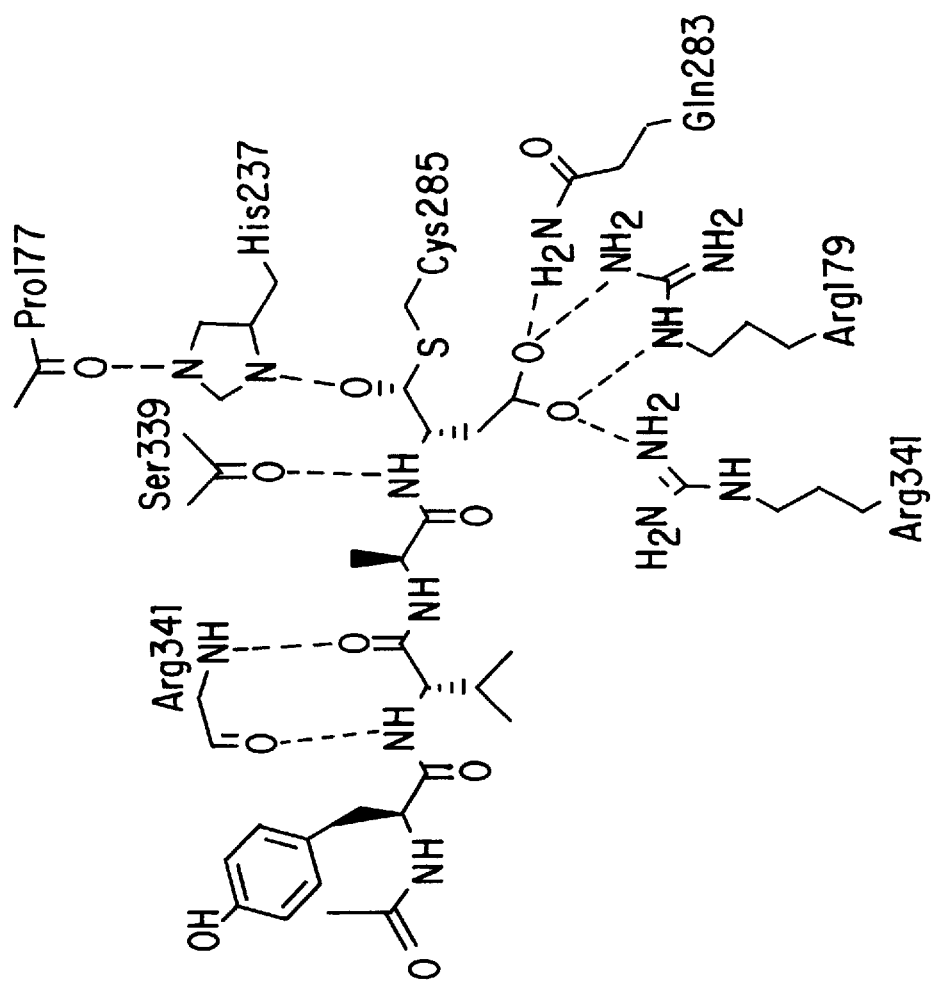
Figure 3B:
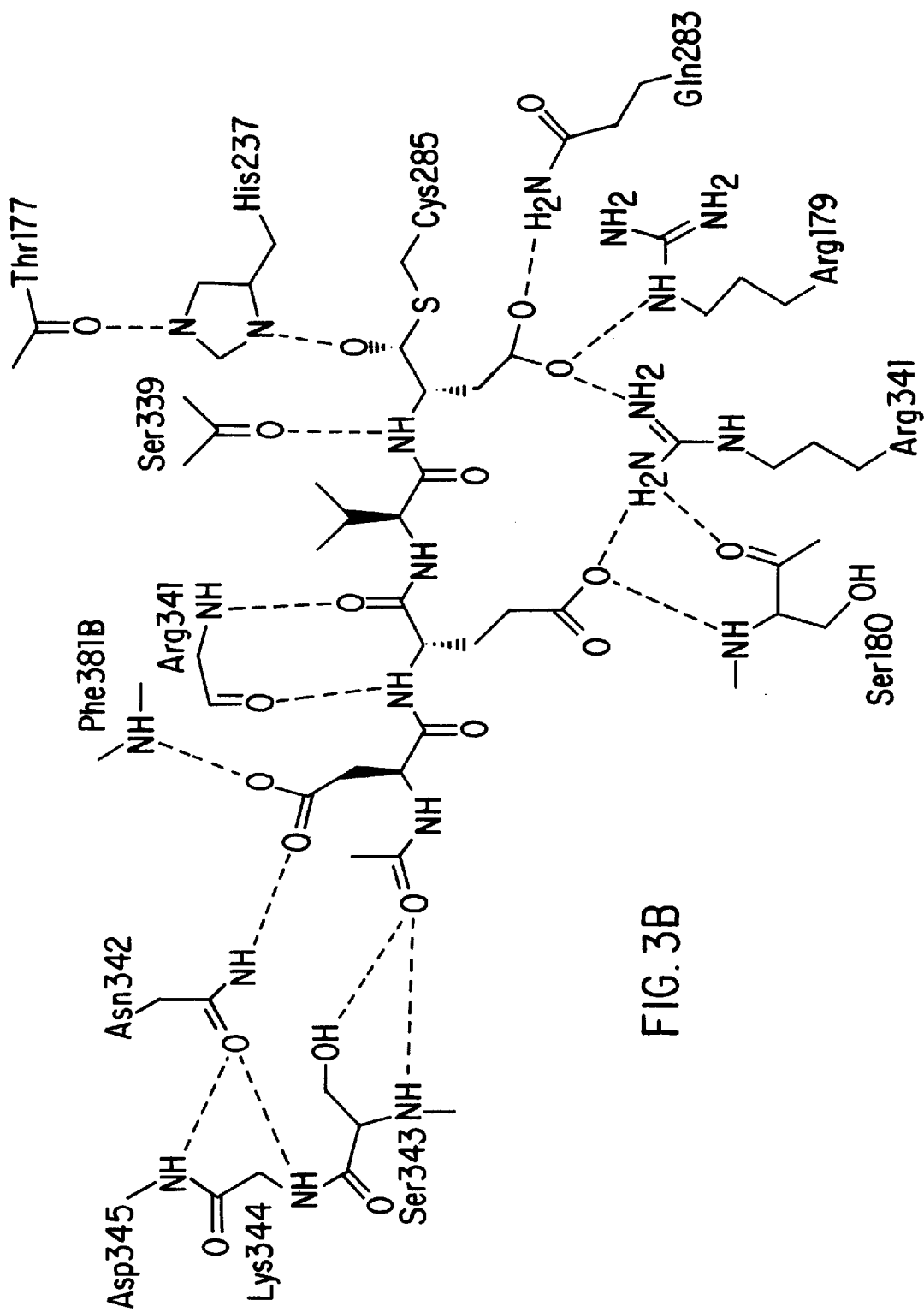

FIG. 3 shows hydrogen bonds and other polar interactions between the bound N-acetyl tetrapeptide aldehyde inhibitor and (A) ICE and (B) apopain.

Figure 4B:
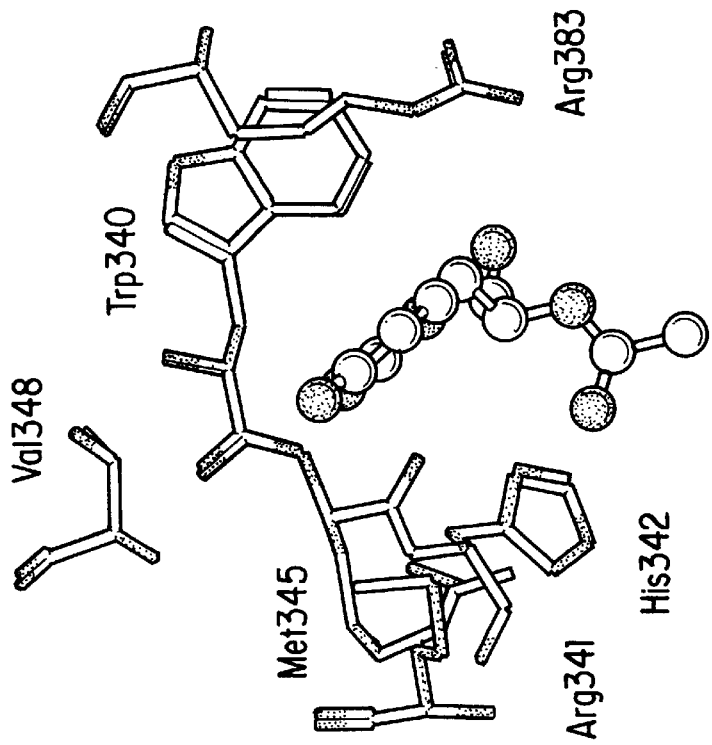
Figure 4A:
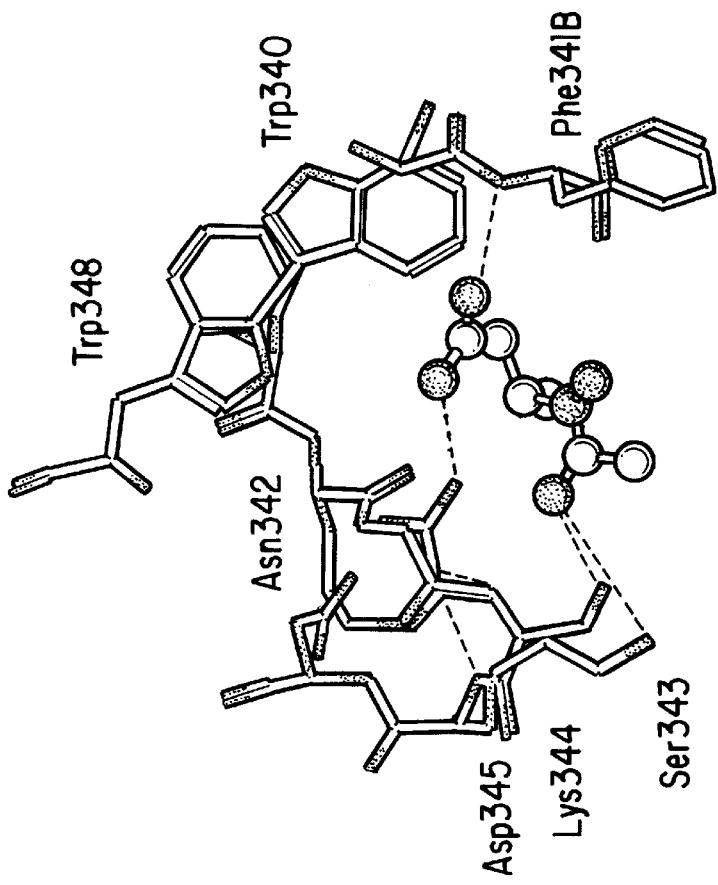

FIG. 4(A) shows the $S_4$ subsite of the apopain:Ac-DEVD-CHO (SEQ ID NO:10) complex. The acetyl group and $S_4$ aspartyl residue of the bound inhibitor are depicted as ball-and-stick models; the protein as rods. Hydrogen bonds are drawn as dashed white lines. FIG. 4(B) shows the $S_4$ subsite of the ICE:YVAD (SEQ ID NO:11) complex. (A) and (B) are oriented to maximize global alignment of the two proteins.

The references cited above are as follows:
1. Ellis, R. E., Yuan, J. Y. & Horvitz, H. R. *Annu Rev Cell Biol* 7, 663–98 (1991).
2. Miura, M., Zhu, H., Rotello, R., Hartwieg, E. A. & Yuan, J. Y. *Cell* 75, 653–660 (1993).
3. Yuan, J. Y., Shaham, S., Ledoux, S., Ellis, H. M. & Horvitz, H. R. *Cell* 75, 641–652 (1993).
4. Thornberry, N. A., et al. *Nature* 356, 768–74 (1992).
5. Cerretti, D. P., et al. *Science* 256, 97–100 (1992).
6. Munday, N. A., et al. *Journal Of Biological Chemistry* 270, 15870–15876 (1995).
7. Faucheu, C., et al. *Embo Journal* 14, 1914–1922 (1995).
8. Kamens, J., et al. *Journal of Biological Chemistry* 270, 15250–15256 (1995).
9. Kumar, S., Kinoshita, M., Noda, M., Copeland, N. G. & Jenkins, N. A. *Genes-Development* 8, 1613–1626 (1994).
10. Wang, L., Miura, M., Bergeron, L., Zhu, H. & Yuan, J. Y. *Cell* 78, 739–750 (1994).
11. Femandes-Alnemri, T., Litwack, G. & Alnemri, E. S. *Journal Of Biological Chemistry* 269, 30761–30764 (1994).
12. Femandes-Alnemri, T., Litwack, G. & Alnemri, E. S. *Cancer Research* 55, 2737–2742 (1995).
13. Femandes-Alnemri, T., et al. *Cancer Research* 55, 6045–6052 (1995).
14. Duan, H., et al. *J. Biol. Chem.* in press (1996).
15. Li, P., et al. *Cell* 80, 401–411 (1995).
16. Kuida, K., et al. *Science* 267, 2000–2003 (1995).
17. Kaufmann, S. H., Desnoyers, S., Ottaviano, Y., Davidson, N. E. & Poirier, G. G. *Cancer-Res* 53, 3976–85 (1993).
18. Lazebnik, Y. A., Kaufmann, S. H., Desnoyers, S., Poirier, G. G. & Earrshaw, W. C. *Nature* 371, 346–347 (1994).
19. Nicholson, D. W., et al. *Nature* 376, 37–43 (1995).
20. Tewari, M., et al. *Cell* 81, 801–9 (1995).
21. Casciola-Rosen, L. A., Miller, D. K., Anhalt, G. J. & Rosen, A. *Journal Of Biological Chemistry* 269, 30757–30760 (1994).
22. Casciola-Rosen, L. A., Anhalt, G. J. & Rosen, A. *J. Exp. Med.* 182, 1625–1634 (1995).
23. Casciola-Rosen, L. A., et al. *J. Exp. Med.* in press (1996).
24. Martin, S. J., et al. *J-Biol-Chem* 270, 6425–8 (1995).
25. Lazebnik, Y. A., et al. *Proceedings Of the National Academy Of Sciences Of the United States Of America* 92, 9042–9046 (1995).
26. Brancolini, C., Benedetti, M. & Schneider, C. *Embo Journal* 14, 5179–5190 (1995).
27. Emoto, Y., et al. *EMBO J.* 14, 6148–6156 (1995).
28. Wilson, K. P., et al. *Nature* 370, 270–275 (1994).
29. Walker, N. P. C., et al. *Cell* 78, 343–352 (1994).
30. Thomberry, N. A., Miller, D. K. & Nicholson, D. W. *Perspectives in Drug Discovery and Design* 2, 389–399 (1995).
31. Engh, R. A., Wright, H. T. & Huber, R. *Protein-Eng* 3, 469–77 (1990).
32. Stein, P. & Chothia, C. *J-Mol-Biol* 221, 615–21 (1991).
33. Frankfater, A. & Kuppy, T. *Biochemistry* 20, 5517–24 (1981).
34. Mackenzie, N. E., Grant, S. K., Scott, A. I. & Malthouse, J. P. *Biochemistry* 25, 2293–8 (1986).
35. Menard, R., et al. *Biochemistry* 30, 8924–8 (1991).
36. *SAINT Software Reference Manual* (Siemens Analytical Instruments, Madison, Wis., 1995).
37. Brunger, A. T. *X-PLOR: Version 3.1, a System for X-Ray Crystallography and NMR* (Yale University Press, New Haven & London, 1992).
38. Abola, E. E., Bernstein, F. C., Bryant, S. H., Koetzle, T. F. & Weng, J. in *Crystallographic Databases—Information Content, Software Systems, Scientific Applications* (eds. Allen, F. H., Bergerhoff, G. & Sievers, R.) 107–132 (Data Commission of the International Union of Crystallography, Bonn/Cambridge/Chester, 1987).
39. Sack, J. S. *J. Mol. Graphics* 6, 224–225 (1988).
40. Zhang, K. Y. J. *Acta Crystallographica Section D Biological Crystallography* 49, 213–222 (1993).
41. Hodel, A., Kim, S.-H. & Brünger, A. T. *Acta Cryst.* A48, 851–858 (1992).
42. Brünger, A. T. *Nature* 355, 472–475 (1992).
43. Frishman, D. & Argos, P. *Proteins—Structure Function and Genetics* 23, 566–579 (1995).

DETAILED DESCRIPTION OF THE INVENTION

In one aspect the present invention is directed to the three-dimensional structure of an isolated and purified enzyme designated apopain and its structure coordinates. Another aspect of the invention is to use the structure coordinates of the apopain crystal to reveal the atomic details of the active site and one or more of the accessory binding sites of apopain. Another aspect of the invention is to use the structure coordinates of an apopain crystal to solve the structure of a different apopain crystal or crystal of a mutant, homologue or co-complex of apopain. A further aspect of the invention is to provide apopain mutants characterized by one or more different properties compared to wild-type apopain. Another aspect of this invention is to use the structure coordinates and atomic details of apopains or mutants or homologues or co-complexes thereof to design, evaluate computationally, synthesize and use modulators of apopain that prevent or treat the undesirable physical and pharmacological properties of apopain. These modulators may be used as therapies that are beneficial in the treatment of immune, proliferative and degenerative diseases including, but not limited to, immune deficiency syndromes (such as AIDS), autoimmune diseases, pathogenic infections, cardiovascular and neurological injury, alopecia, aging, cancer, Parkinson's disease, Alzheimer's disease, Huntington's disease, neurodegenerative disorders and spinal cord injury.

In a second aspect, this invention relates to compounds of formula I (designated L-761,191):

Ac-DEVD-CHO (SEQ ID NO:10)    I useful as research tools in the field of apoptosis, as well as in the treatment of diseases in which reduced apoptosis would be beneficial, including, but not limited to those listed above. In particular, this invention relates to modulators of the pro-apoptotic proteolytic activity of thiol proteinases which cause apoptosis at least in part by disabling the normal biological function of poly(ADP-ribose)polymerase.

Apoptosis constitutes a systematic means of cell suicide within an organism during normal morphogenesis, tissue remodeling as well as in response to pathogenic infections or other irreparable cell damage. Inappropriate apoptosis may underlie the etiology of human diseases such as Alzheimer's, Parkinson's and Huntington's diseases, immune deficiency and autoiminune disorders, ischemic cardiovascular and neurological injury, alopecia, leukemias, lymphomas and other cancers, which therefore makes the control of apoptosis an important potential target for therapeutic intervention.

Several of the biochemical events that contribute to apoptotic cell death have recently been elucidated. Genetic evidence in nematodes, for example, has identified both positive and negative regulators of apoptosis. The key pro-apoptotic gene, ced-3, encodes a putative cysteine protease which is related to mammalian interleukin- 1β converting enzyme (ICE)[6], the first identified member of a new family of cysteine proteases with the distinguishing feature of a near absolute specificity for aspartic acid in the $S_1$ subsite. Deletion or mutation of the ced-3 gene completely prevented the apoptotic death of all cells that were otherwise destined to die, and both CED-3 as well as ICE induced apoptosis when transfected into a variety of host cells. Furthermore, the pro-apoptotic effects of CED-3 could be prevented by co-transfection with the nematode death suppressor gene ced-9 and to some degree by its mammalian counterpart, the proto-oncogene bcl-2. The fate of eucaryotic cells may therefore reside in the balance between the opposing pro-apoptotic effects of an ICE/CED-3-like protease and an upstream regulatory mechanism involving Bcl-2 and/or its homologues.

One of the potential substrates for an ICE/CED-3-like protease during apoptosis is poly(ADP-ribose) polymerase (PARP), a key enzyme in DNA repair, genome surveillance and integrity. PARP is proteolytically cleaved at the onset of apoptosis by a hitherto-unidentified protease with properties that resemble those of ICE. The cleavage site within PARP (DEVD$^{216}$-G$^{217}$) (SEQ ID NO:12) resembles one of the two sites in proIL-1β (FEAD$^{27}$-G$^{28}$) (SEQ ID NO:13) that are recognized and cleaved by ICE. Proteolytic cleavage of PARP at this site results in the separation of the two zinc-finger DNA-binding motifs in the amino-terminus of PARP from the automodification and poly(ADP-ribos)ylating catalytic domains located in the carboxy-terminus of the polypeptide. This cleavage precludes the catalytic domain of PARP from being recruited to sites of DNA damage and presumably disables the ability of PARP to coordinate subsequent repair and genome maintenance events. Furthermore, the Ca$^{2+}$/Mg$^{2+}$-dependent endonuclease implicated in the internucleosomal DNA cleavage that is a hallmark of apoptosis is negatively regulated by poly(ADP-ribos)ylation[20–22]. Loss of normal PARP function would therefore render this nuclease highly activated in dying cells. Other substrates for apopain include the 460 kDa catalytic subunit of DNA-dependent protein kinase (which is essential for double strand DNA break repair and V(D)J recombination) and the 70 kDa protein component of the U1 small ribonucleoprotein (which is necessary for pre-mRNA splicing). The sites of cleavage in all three substrates are at Asp-X-X-Asp (SEQ ID NO:9) motifs, which markedly differs from the preferred recognition motif for ICE (Tyr-X-X-Asp) (SEQ ID NO:14), and in each case results in the physical separation of important functional domains in the target polypeptide. The coordinated disabling of key homeostatic process thus appears to be an underlying principle of apoptotic cell death and an important function of apopain during cell death.

The seven known members of the ICE/CED-3 family of cysteine proteases which are of human origin are ICE, ICE$_{rel}$-II, ICE$_{rel}$-III, ICH-1, CPP32, Mch2 and Mch3. Each is capable of initiating an apoptotic response when transfected into host cells; however, it is possible that overexpression of any protease may cause non-specific induction of cell death. Cytoplasmic expression of other proteases, such as trypsin, chymotrypsin, proteinase K or granzyme B, for example, have also been shown to induce apoptosis[27,28].

In this study we demonstrate that an active form of CPP32, apopain, is the enzyme responsible for the specific proteolytic breakdown of PARP that occurs at the onset of apoptosis. Furthermore, we show that inhibition of apopain-mediated PARP cleavage attenuates apoptosis in vitro, demonstrating the central role played by this protease in the apoptosis of mammalian cells.

In the nematode *C. elegans*, deletion or mutation of a single gene, ced-3, abolishes apoptotic death. When sequenced, ced-3 was found to be homologous to the gene for mammalian interleukin- 1β converting enzyme (ICE), which encodes a protease whose only known function is the cleavage of the inactive 31 kDa proIL- 1β cytokine precursor to the active 17 kDa form. How the apoptotic role of an ICE-like protease in mammalian cells can be accounted for, given the commitment of ICE to IL-1β formation and the finding that apoptosis occurs normally in ICE-deficient mice, has become more obvious with the discovery of four other mammalian ICE/CED-3-like proteases (ICE, ICE$_{rel}$-II, ICE$_{rel}$-III, ICH-1, CPP32, Mch2 and Mch3)[23–26] and the observation that poly(ADP-ribose) polymerase (PARP), a key enzyme in the coordination of genome structure and integrity, is functionally inactivated by a protease resembling ICE (prICE) at the onset of apoptosis. We have demonstrated that prICE is in fact apopain/CPP32 and that apopain/CPP32 is the specific ICE/CED-3-like cysteine protease that cleaves PARP and other substrates at the onset of apoptosis in mammalian cells. The central role played by apopain/CPP32 in mammalian cell death is further substantiated by potent and selective modulators which prevent apoptosis from occurring in vitro. These findings together with the sequence relationship between the apopain proenzyme, CPP32, and CED-3 suggests that CPP32 and its proteolytically active form, apopain, may be the human equivalent of CED-3. The pharmacological modulation of apopain activity may therefore be an appropriate point for therapeutic intervention in pathological conditions where inappropriate apoptosis is prominent.

The cloned apopain cDNA may be recombinantly expressed by molecular cloning into an expression vector containing a suitable promoter and other appropriate transcription regulatory elements, and transferred into prokaryotic or eukaryotic host cells to produce recombinant apopain.

Expression vectors are defined herein as DNA sequences that are required for the transcription of cloned copies of genes and the translation of their mRNAs in an appropriate host. Such vectors can be used to express eukaryotic genes in a variety of hosts such as bacteria, yeast, bluegreen algae, plant cells, insect cells and animal cells.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant apopain in mammalian cells. Commercially-available mammalian expression vectors which may be suitable for recombinant apopain expression, include but are not limited to, pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and lZD35 (ATCC 37565).

DNA encoding apopain may also be cloned into an expression vector for expression in a recombinant host cell. Recombinant host cells may be prokaryotic or eukaryotic, including but not limited to bacteria, yeast, mammalian cells and insect cells. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, infection, protoplast fusion, and electroporation. The expression vector-containing cells are clonally propagated and individually analyzed to determine whether they produce apopain protein. Identification of apopain expressing host cell clones may be done by several means, including but not limited to immunological reactivity with anti-apopain antibodies, and the presence of host cell-associated apopain activity.

Expression of apopain cDNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the apopain cDNA sequence(s) that yields optimal levels of enzymatic activity and/or apopain protein, modified apopain cDNA molecules are constructed. Host cells are transformed with the cDNA molecules and the levels of apopain RNA and protein are measured.

Levels of apopain protein in host cells are quantitated by a variety of methods such as immunoaffinity and/or ligand affinity techniques. apopain-specific affinity beads or apopain-specific antibodies are used to isolate $^{35}$S-methionine labeled or unlabelled apopain protein. Labeled apopain protein is analyzed by SDS-PAGE. Unlabelled apopain protein is detected by Western blotting, ELISA or RIA employing apopain specific antibodies.

Following expression of apopain in a recombinant host cell, apopain protein may be recovered to provide apopain in active form. Several apopain purification procedures are available and suitable for use. Recombinant apopain may be purified from cell lysates or from conditioned culture media, by various combinations of, or individual application of fractionation, or chromatography steps that are known in the art.

In addition, recombinant apopain can be separated from other cellular proteins by use of an immuno-affinity column made with monoclonal or polyclonal antibodies specific for full length nascent apopain or polypeptide fragments of apopain.

The recombinant protein may be used to generate antibodies. The term "antibody" as used herein includes both polyclonal and monoclonal antibodies, as well as fragments thereof, such as, Fv, Fab and F(ab)2 fragments that are capable of binding antigen or hapten.

Monospecific antibodies to apopain are purified from mammalian antisera containing antibodies reactive against apopain or are prepared as monoclonal antibodies reactive with apopain using standard techniques. Monospecific antibody as used herein is defined as a single antibody species or multiple antibody species with homogenous binding characteristics for apopain. Homogenous binding as used herein refers to the ability of the antibody species to bind to a specific antigen or epitope, such as those associated with the apopain, as described above. Enzyme-specific antibodies are raised by immunizing animals such as mice, rats, guinea pigs, rabbits, goats, horses and the like, with rabbits being preferred, with an appropriate concentration of apopain either with or without an immune adjuvant.

Monoclonal antibodies (mAb) reactive with apopain may be prepared by conventional methods, such as by immunizing inbred mice with apopain. The mice are immunized with about 0.1 mg to about 10 mg, preferably about 1 mg, of apopain in about 0.5 ml buffer or saline incorporated in an equal volume of an acceptable adjuvant. Freund's complete adjuvant is preferred. The mice receive an initial immunization on day 0 and are rested for about 3 to about 30 weeks. Immunized mice are given one or more booster immunizations of about 0.1 to about 10 mg of apopain in a buffer solution such as phosphate buffered saline (PBS) by the intravenous (IV) route. Lymphocytes from antibody-positive mice are obtained by removing spleens from immunized mice by standard procedures known in the art. Hybridoma cells are produced by mixing the splenic lymphocytes with an appropriate fusion partner under conditions which will allow the formation of stable hybridomas. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using apopain as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

In vitro production of anti-apopain is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of apopain in body fluids or tissue and cell extracts.

Methods such as those described above may be used to produce monospecific antibodies may be utilized to produce antibodies specific for apopain polypeptide fragments or full-length nascent apopain polypeptide.

Apopain antibody affinity columns are made by adding the antibodies to a gel support, such as Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing apopain or apopain fragments are slowly passed through the column. The column is then washed, and the protein is eluted. The purified apopain protein is then dialyzed against phosphate buffered saline.

Kits containing apopain cDNA, antibodies to apopain or apopain protein may be prepared. Such kits are used to detect DNA which hybridizes to apopain DNA or to detect the presence of apopain protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of apopain DNA, apopain RNA or apopain protein. The recombinant proteins, DNA molecules, RNA molecules and antibodies lend themselves to the formulation of kits suitable for the detection and typing of apopain. Such a kit would comprise a compartmentalized carrier suitable to hold in close confinement at least one container. The carrier would further comprise reagents such as recombinant apopain protein or anti-apopain antibodies suitable for detecting apopain. The carrier may also contain means for detection such as labeled antigen or enzyme substrates or the like.

Nucleotide sequences that are complementary to the apopain encoding cDNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other apopain antisense oligonucleotide mimetics. Apopain antisense molecules may be introduced into cells by microinjection, liposome encapsulation or by expression from vectors harbouring the antisense sequence. apopain antisense therapy may be particularly useful for the treatment of diseases where it is beneficial to reduce apopain activity.

Apopain gene therapy may be used to introduce apopain into the cells of target organs. The apopain gene can be ligated into viral vectors which mediate transfer of the apopain DNA by infection of recipient host cells. Suitable viral vectors include retrovirus, adenovirus, adeno-associated virus, herpes virus, vaccinia virus, polio virus and the like. Alternatively, apopain DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations of them are suitable for ex vivo as well as in vivo apopain gene therapy. Apopain gene therapy may be particularly useful for the treatment of diseases where it is beneficial to elevate apopain activity.

Pharmaceutically useful compositions comprising apopain DNA or apopain protein may be formulated as described elsewhere in this application or according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein or DNA.

Therapeutic or diagnostic compositions of the invention are administered to an individual in amounts sufficient to treat or diagnose apopain related disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate.

As used herein, a "functional derivative" of apopain is a compound that possesses a biological activity (either functional or structural) that is substantially similar to the biological activity of apopain. The term "functional derivatives" is intended to include the "fragments," "variants," "degenerate variants," "analogs" and "homologues" or to "chemical derivatives" of apopain. The term "fragment" is meant to refer to any polypeptide subset of apopain. The term "variant" is meant to refer to a molecule substantially similar in structure and function to either the entire apopain molecule or to a fragment thereof. A molecule is "substantially similar" to apopain if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire apopain molecule or to a fragment thereof.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

The present invention is also directed to methods for screening for compounds which modulate that expression of DNA or RNA encoding apopain as well as the function of apopain protein in vivo. Compounds which modulate these activities may be DNA, RNA, peptides, proteins, or nonproteinaceous organic molecules. Compounds may modulate by increasing or attenuating the expression of DNA or RNA encoding apopain or the function of apopain protein. Compounds that modulate the expression of DNA or RNA encoding apopain or the function of apopain protein may be detected by a variety of assays. The assay may be a simple "yes/no" assay to determine whether there is a change in expression or function. The assay may be made quantitative by comparing the expression or function of a test sample with the levels of expression or function in a standard sample.

In a second aspect, the invention encompasses compounds of formula I (L-761,191):

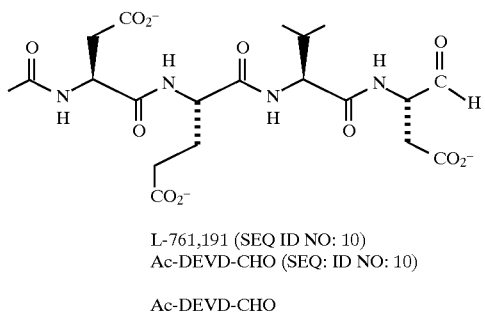

L-761,191 (SEQ ID NO: 10)
Ac-DEVD-CHO (SEQ: ID NO: 10)

Ac-DEVD-CHO or a pharmaceutically acceptable salt thereof.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, ammonium, potassium, sodium, zinc and the like. Particularly preferred are the calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The ability of the compounds of Formula I to inhibit the action of apopain make them useful research tools in the field of apoptosis. These compounds are also useful to treat, prevent, or ameliorate in mammals and especially in humans, diseases including but not limited to:

1. immune deficiency syndrome (including AIDS)
2. type I diabetes
3. pathogenic infections
4. cardiovascular and neurological injuries
5. alopecia
6. aging
7. Parkinson's disease
8. Alzheimer's disease Dose Ranges The magnitude of therapeutic dose of a compound of Formula I will, of course, vary with the nature of the severity of the condition to be treated and with the particular compound of Formula VI and its route of administration and vary upon the clinician's judgment. It will also vary according to the age, weight and response of the individual patient. An effective dosage amount of the active component can thus be determined by the clinician after a consideration of all the criteria and using is best judgment on the patient's behalf.

An ophthalmic preparations for ocular administration comprising 0.001–1% by weight solutions or suspensions of the compounds of Formula I in an acceptable ophthalmic formulation may be used.

Pharmaceutical Compositions

Any suitable route of administration may be employed for providing a mammal, especially a human with an effective dosage of a compound of the present invention. For example, oral, parenteral and topical may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, parenteral and ocular (ophthalmic). They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, alcohols, oils, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case or oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil emulsion. Such compositions may be prepared by any of the methods of pharmacy but all methods include the step of bringing into active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Compounds of the instant invention are conveniently prepared using procedures known in the art.

Proteolytic cleavage of poly(ADP-ribose)polymerase may be measured as followed.

(a) Preparation of [$^{35}$S] radiolabelled PARP

The cDNA encoding human poly(ADP-ribose) polymerase (clone pCD-12; GenBank accession no. M32721; NCBI gi 190266) was excised from its cloning vector by Xho I restriction digestion then ligated into Xho I-cut, CIP-treated pBluescript II SK+ (Stratagene). Following transformation into competent *Escherichia coli* cells, colony purification and propagation of the resulting transformed cells in liquid culture, the plasmid DNA was purified and the orientation of the PARP cDNA was determined by restriction enzyme analysis. Clones oriented in the T7 as well as T3 directions were obtained and their plasmid DNA was used to direct the synthesis of [$^{35}$S]PARP by coupled in vitro transcription/translation using TnT reticulocyte lysates (Promega) in the presence of [$^{35}$S]methionine (New England Nuclear). The resulting [$^{35}$S]PARP polypeptide was purified away from the constituents of the reticulocyte lysate mixture by gel filtration chromatography on a Superdex-75 HR 10/30 column (Pharmacia) which had been equilibrated in 10 mM Hepes/KOH (pH 7.4), 2 mM EDTA, 0.1% CHAPS, 5 mM dithiothreitol.

(b) Measurement of PARP cleavage

Incubation mixtures (25 μl final volume) were prepared in a buffer composed of 10 mM Hepes/KOH (pH 7.4), 2 mM EDTA, 0.1% CHAPS, 5 mM dithiothreitol and contained 5 μl of purified [$^{35}$S]PARP, 0–10 μl of PARP cleavage activity (e.g.., fractions from apoptotic osteosarcoma,THP-1 or other cells, or purified apopain or recombinant apopain) plus drug, where indicated, or vehicle. The mixtures were incubated for 60 min at 37° C. then terminated by the addition of 6.5 μl of 5-fold concentrated SDS-containing PAGE sample buffer followed by denaturation for 5 min at 95° C. The samples were resolved on 10% polyacrylamide gels, transferred to a poly(vinylidene difluoride) membrane by electroblotting, then the [$^{35}$S]PARP cleavage products were visualized by autoradiography. PARP cleavage was measured as the breakdown of the 113.1 kDa PARP polypeptide into 24.1 kDa and 89.1 kDa fragments. PARP cleavage activity was quantified by the volume-density of the 24.1 kDa fragment as determined by laser densitometry of the resulting autoradiogram.

(c) Measurement of PARP cleavage by cleavage of a fluorogenic substrate

A fluorogenic derivative of the tetrapeptide recognized by apopain and corresponding to the $P_1$ to $P_4$ amino acids of the PARP cleavage site, Ac-DEVD-AMC (AMC, amino-4-methylcoumarin) was prepared as follows: i) synthesis of N-Ac-Asp(OBn)-Glu(OBn)-Val-CO$_2$H, ii) coupling with Asp(oBn)-7-amino-4-methylcoumarin, iii) removal of benzyl groups.

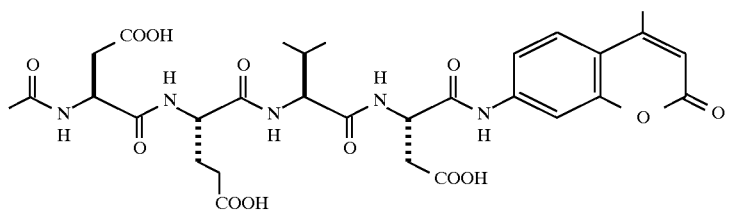

50

Standard reaction mixtures (300 μl final volume), contained Ac-DEVD-AMC and purified or crude PARP-cleavage apopain/CPP32 enzyme in 100 mM Hepes/KOH (pH 7.5), 10% (w/v) sucrose, 0.1% (w/v) CHAPS, 10 mM dithiothreitol, and were incubated at 25° C. Reactions were monitored continuously in a spectrofluorometer at an excitation wavelength of 380 nm and an emission wavelength of 460 nm.

Preparation of Crystals and X-ray Crystallography

The term "structure coordinates" refers to mathematical coordinates derived from mathematical equations related to the patterns obtained on diffraction of a monochromatic beam of X-rays by the atoms (scattering centers) of an apopain molecule in crystal form. The diffraction data are used to calculate an electron density map of the repeating unit of the crystal. The electron density maps are used to establish the positions of the individual atoms within the unit cell of the crystal.

The term "heavy atom derivatization" refers to the method of producing a chemically modified form of the crystal of apopain. A crystal is soaked in a solution containing heavy metal atom salts or organometallic compounds, which can diffuse through the crystal and bind to the surface of the protein. The location(s) of the bound heavy metal atom(s) are determined by X-ray diffraction analysis of the soaked crystal. This information is used to generate the phase information used to construct three-dimensional structure of the protein.

Those of skill in the art understand that a set of structure coordinates determined by X-ray crystallography is not without standard error.

The term "unit cell" refers to the basic parallelipiped shaped block. The entire volume of a crystal may be constructed by regular assembly of such blocks.

The term "space group" refers to the arrangement of symmetry elements of a crystal.

The term "molecular replacement" refers to a method that involves generating a preliminary model of an apopain crystal whose structure coordinates are not known, by orienting and positioning a molecule whose structure coordinates are known. Phases are then calculated from this model and combined with observed amplitudes to give an approximate Fourier synthesis of the structure whose coordinates are known.

The structure coordinates of apopain may be used to design compounds that bind to the enzyme and alter its physical properties in a variety of ways. The structure coordinates of the enzyme may also be used to screen computationally small molecule data bases for compounds that bind to the enzyme. The structure coordinates of apopain mutants may also facilitate the identification of related proteins or enzymes, thereby further leading to novel therapeutic modes for treating or preventing apopain-mediated conditions.

The following examples illustrate the present invention without, however, limiting the same thereto.

EXAMPLE 1

Production of Apopain

The method used for production of apopain involves folding of active enzyme from its constituent p17 and p12 subunits which are expressed separately in *E. coli*. The apopain/CPP32 p17 subunit ($Ser^{141}$-$Asp^{297}$) and p12 subunit ($Ser^{310}$-$His^{402}$) were engineered for expression as $MetSer^{141}$-$Asp^{297}$ and $MetSer^{310}$-$His^{402}$ constructs, respectively, by PCR-directed template modification. A cDNA encoding the p17 subunit was amplified with the sense (forward) synthetic oligonucleotide 5'- GCT CTA GAC TCG AGT CAT GAG TGG AAT ATC CCT GGA CAA CAG TTA TAA AAT GG -3' (SEQ ID NO:5) plus the antisense (reverse) oligonucleotide 5'- GCT CTA GAC TCG AGT CAT GAT TAG TCT GTC TCA ATG CCA CAG TCC AGT TCT G -3' (SEQ ID NO:6) using the full length CPP32β cDNA (3 ng/μl) as template (Pwo polymerase (0.025 U/μl) Boehringer Mannheim; 25 cycles of 1 min at 94° C., 1 min at 60° C., 45 sec at 72° C.). A cDNA encoding the p12 subunit was amplified the same way except that the sense (forward) oligonucleotide was 5'- GCT CTA GAC TCG AGT CAT GAG TGG TGT TGA TGA CAT GGC GTG TC -3' (SEQ ID NO:7) and the antisense (reverse) oligonucleotide was 5'- GCT CTA GAC TCG AGT CAT GAT TAG TGA TAA AAA TAG AGT TCT TTT GTG AGC -3'. (SEQ ID NO:8) The resulting PCR fragments were purified, trimmed with Xba I then ligated into the Xba I site of pBluescript II SK(+) (Stratagene). Following sequence verification, inserts were excised from nested Bsp HI sites and ligated into the Nco I site of pET-11d (Novagen). Appropriately oriented clones were then transformed into *E. coli* BL21 (DE3)pLysS cells. Optimal growth conditions for production cultures employed M9 medium at 37° with overnight induction using 1 mM IPTG for expression of the recombinant proteins. (Under these conditions, the individual subunits were expressed at approximately 50 mg/liter. In both cases the protein was localized exclusively in the inclusion body fraction where they generally constituted >99% of the total protein.) The *E. coli* were harvested, washed, and broken in the presence of protease inhibitors. The inclusion bodies were then isolated and solubilized in 6M guanidine-hydrochloride. In order to generate active recombinant apopain, the denatured p17 and p12 subunits were mixed and rapidly diluted to a concentration of 100 μg/ml in 100 mM HEPES/KOH (pH 7.5) 10% (w/v) sucrose, 0.1% (w/v) CHAPS, 0.5M NaCl, 10 mM DTT. (Several pilot experiments have established these to be the optimal folding conditions.) The reactions were then incubated at room temperature for 60 min. Under these conditions some of the subunit protein precipitated; this was removed by ultracentrifugation at 100,000×g for 60 min. Using this method, the efficiency of refolding was approximately 10% (mole active enzyme/mole p17 subunit×100%) which corresponds to a total yield of approximately 5 mg active enzyme/liter culture.

EXAMPLE 2

Purification of Apopain

The active enzyme was subsequently separated from incorrectly folded protein by anion-exchange chromatography using a 1 ml HiTrap Q column (Pharmacia). Mass spectral analysis of recombinant apopain complex indicates that it comprises intact p17 chains, spanning $Ser^{141}$ to $Asp^{297}$, and a mixture of p12 chains, consisting of predominantly $MetSer^{310}$-$His^{402}$ with some $Ser^{310}$-$His^{402}$. The resulting enzyme is indistinguishable from native enzyme with regard to kinetic parameters for inhibition by Ac-DEVD-CHO (SEQ ID NO:10).

EXAMPLE 3

Crystallization of Apopain

The apopain:Ac-DEVD-CHO (SEQ ID NO:10) complex was crystallized by hanging-drop vapor diffusion. 1.5 μl drops of protein-inhibitor solution (8.7 mg/ml in 10 mM Tris-HCl pH 8.5, 10 mM DTT, 3 mM $NaN_3$) were mixed with an equal volume of reservoir buffer (7% PEG-6000 (w/w), 0.10M sodium citrate pH 5.0, 10 mM DTT, 3 mM $NaN_3$) and incubated at room temperature. The crystals belong to the orthorhombic space group I222 with a=69.81, b=84.62, c=96.79 Å.

EXAMPLE 4

Structure Solution and Refinement

Three-dimensional diffraction data extending to a resolution of 2.5 Å were collected at room temperature using a Siemens area detector and CuKα radiation from a Rigaku RU-200 rotating-anode X-ray generator. These data were processed with the SAINT software package[36]. 20,801 observations of 8,929 unique reflections were merged with an R-factor of 5.55%. The structure was solved by molecular replacement, using X-PLOR[37] and a model based on PDB[38] entry 1ICE, the structure of inhibited ICE[28]. The current model was constructed by interactive model-building[39] and refinement using X-PLOR[37]. In early stages of model-building, phase refinement using SQUASH[40] significantly improved the quality of electron density maps. The current model was inspected against 10% simulated-annealing omit maps[41] and comprises residues 149–295 of the p17 chain, residues 317–402 of the p12 chain, the bound inhibitor, and 25 ordered water molecules. Residues 141–148 at the N-terminus of the p17 chain, 296–297 at the C-terminus of the p17 chain, and 310–316 at the N-terminus of the p12 chain are not visible in the current electron density maps, presumably due to disorder. The R-factor of the refined model is 26.2% ($R_{free}$=34.2%)[42] and the stereochemistry is reasonable (r.m.s. deviation of bonds=0.006 Å, angles= 1.3°). Secondary structures were assigned to both apopain and ICE using the program STRIDE[43]. Special care was taken to establish the chirality at the optical center created by the nucleophilic attack of $Cys^{285}$ Sγ at the $P_1$ carbon atom.

After refinement was completed, equivalent models were constructed for each possible configuration at this atom and the two models were refined in parallel with chiral restraints that were identical in magnitude, but opposite in hand. Then, all atoms within 8.0 Å of this atom were deleted from each model and both truncated models were subjected to a 3000K simulated-annealing refinement. Electron density maps of this part of the complex were then calculated from both sets of phases and inspected to determine the stereochemistry at this site. The coordinates and structure factors of the apopain:Ac-DEVD-CHO (SEQ ID NO:10) complex will be deposited in the Protein Data Bank[38].

What is claimed:

1. A method of identifying inhibitors of apopain by rational drug design comprising:
   (a) designing a potential inhibitor for apopain that will form non-covalent bonds with amino acids in the apopain substrate binding site based upon the crystal structure co-ordinates of apopain:Ac-DEVD-CHO (SEQ ID No:10) complex;
   (b) synthesizing the inhibitor; and
   (c) determining whether the potential inhibitor inhibits the activity of apopain.

2. The method of claim 1 wherein the crystal structure co-ordinates of the apopain:Ac-DEVD-CHO (SEQ ID No:10) complex are obtained from an apopain:Ac-DEVD-CHO (SEQ ID No:10) complex crystal having orthorhombic space group symmetry I222 with a=69.81, b=84.62, and c=96.79 Å.

3. The method of claim 2 wherein the co-ordinates of the apopain:Ac-DEVD-CHO (SEQ ID No:10) complex are obtained by means of computational analysis.

4. The method of claim 1 wherein the potential inhibitor is designed to form hydrogen bonds with $Ser^{339}$ and $Arg^{341}$ of apopain.

5. The method of claim 1 wherein the potential inhibitor is designed to have a carbonyl carbon atom that binds to the $S\gamma$ of $Cys^{285}$ of apopoain.

6. The method of claim 1 wherein the potential inhibitor is designed to have a Glu at the $P_3$ position that forms a salt link with $Arg^{341}$ of apopain.

7. The method of claim 1 wherein the potential inhibitor is designed to have a Val at the $P_2$ position that lies against a hydrophobic wall of a groove centered on the side chain of $Tyr^{338}$ of apopain.

8. The method of claim 1 wherein the potential inhibitor is designed to have a carboxyl group that makes specific polar interactiosn with the amide nitrogen atom of $Phe^{381B}$ and the $N^{\delta 1}$ atom of $Asp^{342}$ of apopain.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GCTCTAGACT  CGAGTCATGA  GTGGAATATC  CCTGGACAAC  AGTTATAAAA  TGG          53
```

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GCTCTAGACT  CGAGTCATGA  TTAGTCTGTC  TCAATGCCAC  AGTCCAGTTC  TG           52
```

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GCTCTAGACT  CGAGTCATGA  GTGGTGTTGA  TGATGACATG  GCGTGTC                  47
```

( 2 ) INFORMATION FOR SEQ ID NO:4:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCTCTAGACT CGAGTCATGA TTAGTGATAA AAATAGAGTT CTTTTGTGAG C  51

( 2 ) INFORMATION FOR SEQ ID NO:5:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GCTCTAGACT CGAGTCATGA GTGGAATATC CCTGGACAAC AGTTATAAAA TGG  53

( 2 ) INFORMATION FOR SEQ ID NO:6:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GCTCTAGACT CGAGTCATGA TTAGTCTGTC TCAATGCCAC AGTCCAGTTC TG  52

( 2 ) INFORMATION FOR SEQ ID NO:7:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GCTCTAGACT CGAGTCATGA GTGGTGTTGA TGATGACATG GCGTGTC  47

( 2 ) INFORMATION FOR SEQ ID NO:8:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: Other ( x i ) SEQUENCE DESCRIPTION: SEQ ID NO:8:

GCTCTAGACT CGAGTCATGA TTAGTGATAA AAATAGAGTT CTTTTGTGAG C  51

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Asp Xaa Xaa Asp
1

( 2 ) INFORMATION FOR SEQ ID NO:10:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

Asp Glu Val Asp
1

( 2 ) INFORMATION FOR SEQ ID NO:11:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Tyr Val Ala Asp
1

( 2 ) INFORMATION FOR SEQ ID NO:12:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Asp Glu Val Asp Gly
1       5

( 2 ) INFORMATION FOR SEQ ID NO:13:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

Phe Glu Ala Asp Gly
1       5

( 2 ) INFORMATION FOR SEQ ID NO:14:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:14:

Tyr Xaa Xaa Asp
1